United States Patent [19]

Wonderley

[11] Patent Number: 5,417,704

[45] Date of Patent: May 23, 1995

[54] DISPOSABLE SURGICAL SCALPEL WITH SAFETY GUARD

[75] Inventor: Jeff W. Wonderley, Ft. Defiance, Va.

[73] Assignee: American Safety Razor Company, Verona, Va.

[21] Appl. No.: 169,040

[22] Filed: Dec. 20, 1993

Related U.S. Application Data

[63] Continuation-in-part of Ser. No. 986,741, Dec. 8, 1992, Pat. No. 5,309,641, which is a continuation-in-part of Ser. No. 808,891, Dec. 18, 1991, Pat. No. 5,299,357.

[51] Int. Cl.⁶ ............................................. A61B 17/32
[52] U.S. Cl. ..................................... 606/167; 30/162; 30/335
[58] Field of Search ................... 606/167–170, 606/172, 166; 30/2, 151, 162, 335; 128/751

[56] References Cited

U.S. PATENT DOCUMENTS

| | | |
|---|---|---|
| 2,304,332 | 12/1942 | Bodkin . |
| 3,412,467 | 11/1968 | Matwijcow . |
| 3,889,368 | 6/1975 | Himeno . |
| 3,905,101 | 9/1975 | Shepherd . |
| 3,906,626 | 9/1975 | Riuli . |
| 4,491,132 | 1/1985 | Aikins ................................ 606/167 |
| 4,523,379 | 6/1985 | Osterhout et al. . |
| 4,576,164 | 3/1986 | Richeson . |
| 4,719,915 | 1/1988 | Porat et al. . |
| 4,735,202 | 4/1988 | Williams . |
| 4,768,509 | 9/1968 | Grosvenor et al. . |
| 4,803,751 | 2/1989 | Cousins . |
| 4,958,625 | 9/1990 | Bates et al. . |
| 4,985,034 | 1/1991 | Lipton . |
| 5,071,426 | 12/1991 | Dolgin et al. . |
| 5,139,507 | 8/1992 | Dolgin et al. . |
| 5,201,748 | 4/1993 | Newman et al. . |
| 5,250,063 | 10/1993 | Abidin et al. ..................... 606/167 |

FOREIGN PATENT DOCUMENTS

| | | | |
|---|---|---|---|
| 3722899 | 1/1989 | Germany | 606/167 |
| 9011725 | 10/1990 | WIPO | 606/167 |

Primary Examiner—Stephen C. Pellegrino
Assistant Examiner—William W. Lewis
Attorney, Agent, or Firm—Willian Brinks Hofer Gilson & Lione

[57] ABSTRACT

A scalpel including an elongated handle having an engaging surface located on the handle, a blade carried by the handle adjacent one end thereof and a guard movably mounted to the handle for sliding movement relative to the handle between a protective position covering the blade and a retracted position exposing the blade for use. The guard includes side members extending downwardly from an upper surface. The side members are positioned adjacent opposite sides of the handle and the resiliency of the guard forces the inner surfaces of the side members into engagement with the engaging surface of the handle. The guard is movably along the engaging surface in response to sliding movement of the guard relative to the handle. In a further form, the guard is slidable into a permanently locked position relative to the handle, thereby preventing reuse of the scalpel and inadvertent exposure of the blade. In yet a further form, a locking means requires a force substantially perpendicular to the axis of motion of the guard to release the guard from the temporary protective position.

18 Claims, 11 Drawing Sheets

DISPOSABLE SURGICAL SCALPEL WITH SAFETY GUARD

This application is a Continuation-In-Part of application Ser. No. 07/986,741, filed Dec. 8, 1992, now U.S. Pat. No. 5,309,641, which is a Continuation-In-Part of application Ser. No. 07/808,891, now U.S. Pat. No. 5,299,357, filed Dec. 18, 1991.

BACKGROUND OF THE INVENTION

The present invention relates to a surgical scalpel and particularly relates to a scalpel having a guard movable along the scalpel handle and blade between a protective position temporarily overlying and covering the blade and a retracted position exposing the blade for use. The invention also relates to a scalpel wherein the guard may additionally be moved into a permanent protective position permanently covering and overlying the blade.

Disposable scalpels are well known in the art and often comprise a handle, typically formed of a plastic material, to which is attached either permanently or detachably, a scalpel blade. Such disposable scalpels are conventionally packaged in sterile containers, e.g., flexible plastic packages or pouches. Once removed from the container, the blade is typically exposed for use. This, of course, also exposes the blade to all individuals, doctors, nurses, medical technicians, etc., associated with a surgical procedure, as well as those individuals charged with the disposal of the used scalpel. Thus, even with the exercise of great care, individuals are frequently inadvertently cut by the exposed blade. The dangers of being cut and transmission of infectious diseases when cut by a used blade are thus ever-present. Even when using scalpels having blades which are detached after use and disposed in a sharps container, those individuals handling the scalpels, blades or sharps containers remain at risk.

Scalpels having sheaths affording individuals protection against being cut by exposed blades are known in the prior art. For example, in U.S. Pat. No. 3,906,626, there is disclosed a sheath for a scalpel which is movable between a retracted position, exposing the blade for use, and an extended position, substantially wholly enclosing the blade.

This scalpel also provides a sheath movable into a third and permanently locked position overlying the blade, whereby the blade cannot be reused and individuals, including those charged with the disposal of the blade, are protected from being cut by the blade. This scalpel, however, has many drawbacks. The blade lacks stability in the hands of the surgeon because the sheath completely overlies the handle in the retracted position of the sheath which corresponds to the use position of the scalpel. That is, the surgeon must grasp the sheath, not the handle, in order to use the scalpel. There is accordingly a danger of play between the sheath and the handle when the scalpel is used by the surgeon. Further, two hands are necessary to displace this sheath between a position exposing the blade for use and its protective position. These and other disadvantages of the scalpel disclosed in that patent will become apparent from reference to the following description of the present invention.

SUMMARY OF THE INVENTION

According to the present invention, there is provided a novel and improved disposable scalpel or knife, comprising an elongated handle having an engaging surface located on the handle, a blade permanently secured adjacent one end of the handle and a guard movably mounted to the handle for sliding movement relative to the handle between a temporary protective position covering the blade and a retracted position exposing the blade for use. The guard is an integrally molded piece of plastic formed in a U-shaped channel which comprises a pair of side members extending downwardly from an upper surface. The side members are positioned adjacent opposite sides of the handle, wherein the resiliency of the guard forces a guide arm on each side member into engagement with the engaging surface on the handle. The resiliency of the guard prevents the side members from spreading apart and thereby prevents the removal of the guard from the handle. The guard is movable along the engaging surface in response to sliding movement of the guard relative to the handle between the protective and retracted positions. Furthermore, the scalpel comprises a locking means for releasably maintaining the guard in the temporary protective position and the retracted position.

In another embodiment of the present invention, the locking means further comprises a wedge disposed on the engaging surface and a latch disposed on the guide arm of the side members so as to allow the guard to be positioned in a permanently protective position.

To locate the guard into the protective position permanently covering the blade, the guard is moved forwardly past the temporary protective position and against the bias of the wedge located at the forward end of the engaging surface on the handle. Upon displacing the latch on the guard arm forward of the wedge, the wedge engages the latch so as to prevent rearward movement of the guard. As a result, the guard is locked in the permanent protective position.

In yet another embodiment of the present invention, the locking means requires a force substantially perpendicular to the axis of motion of the guard to release the guard from the temporary protective position.

In all of the aforementioned embodiments, the lower surface of the handle is completely exposed and the upper surface of the handle is partially exposed in all positions of the guard. Furthermore, when the guard is in the retracted position, the upper surface of the guard and the upper surface of the handle form a continuous upper surface. Moreover, the handle comprises a receiving cavity which contributes to the prevention of pivotal movement of the guard relative to the handle in the plane of the handle. As a result, when the guard is in the retracted position, the upper surface of the scalpel operates as a single non-disjoint surface. It will also be appreciated from the ensuing description and drawings that the guide arms are shaped for cooperation with the engaging surface on the handle so as to maintain the guard in positions straddling the handle in all positions of the guard along the handle. In other words, the guide arms and engaging surface also cooperate to prevent the guard from pivoting in the plane of the handle.

The scalpel of the present invention affords various additional advantages and features in comparison with conventional scalpels including those with protective sheaths. For example, a surface of the handle of the scalpel, as discussed previously, is fully exposed in all positions of the guard so that control of the cutting edge by the surgeon may be maintained by direct finger contact with the scalpel handle during use. Moreover, the guard is slidable along the handle between all positions using only one hand. It does not require two hands to move the guard between its protective and retracted positions. Further, the guard is slidable between retracted and temporary protective positions multiple times, whereby the scalpel may be used, set aside with the guard in its temporary protective position, and then reused with the guard movable again into its retracted position. Still further, the construction of the handle and guard may be of all plastic material whereby the scalpel may be formed and assembled inexpensively.

Accordingly, it is a primary object of the present invention to provide a novel and improved disposable scalpel with a guard movable between a retracted position exposing the scalpel blade for use, a temporary protective position overlying and covering the blade, protecting individuals from the blade, and a permanent protective position overlying and covering the blade, whereby the guard cannot be removed from its permanent protective position without effectively destroying the scalpel or the guard.

These and further objects and advantages of the present invention will become more apparent upon reference to the following specification, appended claims and drawings.

BRIEF DESCRIPTION OF THE DRAWING FIGURES

DETAILED DESCRIPTION OF THE DRAWING FIGURES

Reference will now be made in detail to a present preferred embodiment of the invention, an example of which is illustrated in the accompanying drawings.

Figure 1:
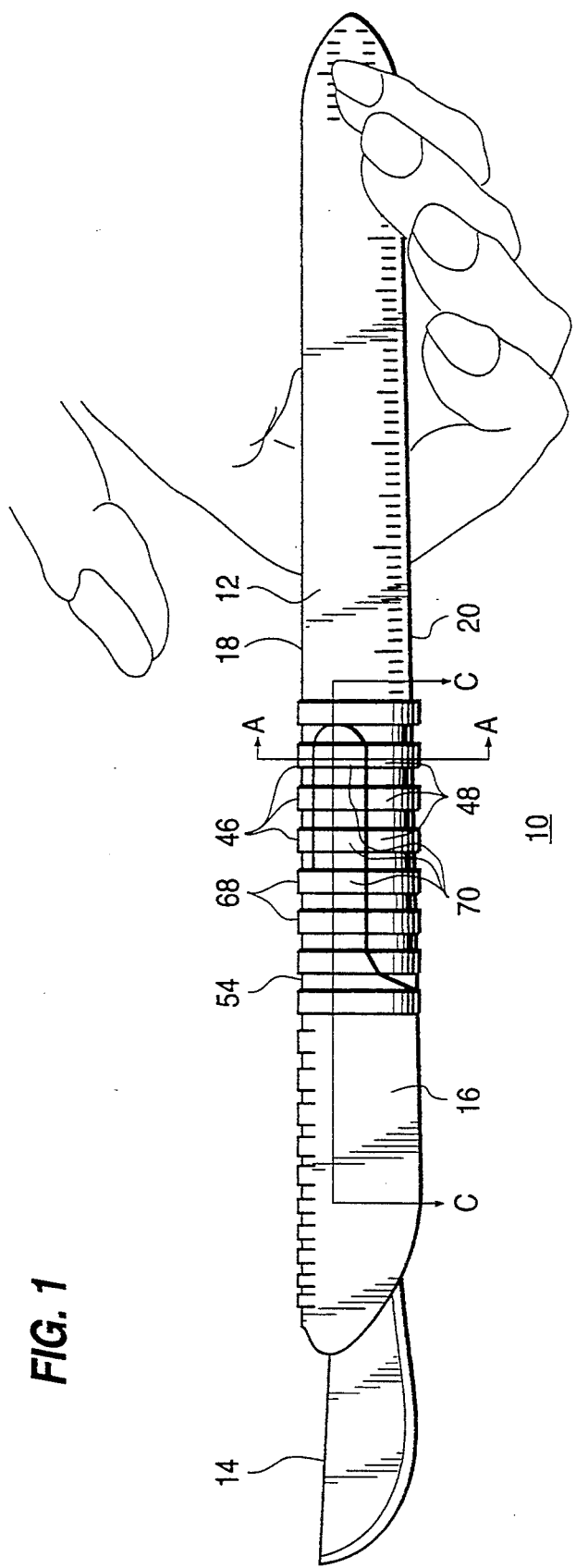
FIG. 1 is a side elevational view of a disposable scalpel with guard constructed in accordance with the present invention and illustrating the guard in a retracted position exposing the blade for use.
Figure 7:
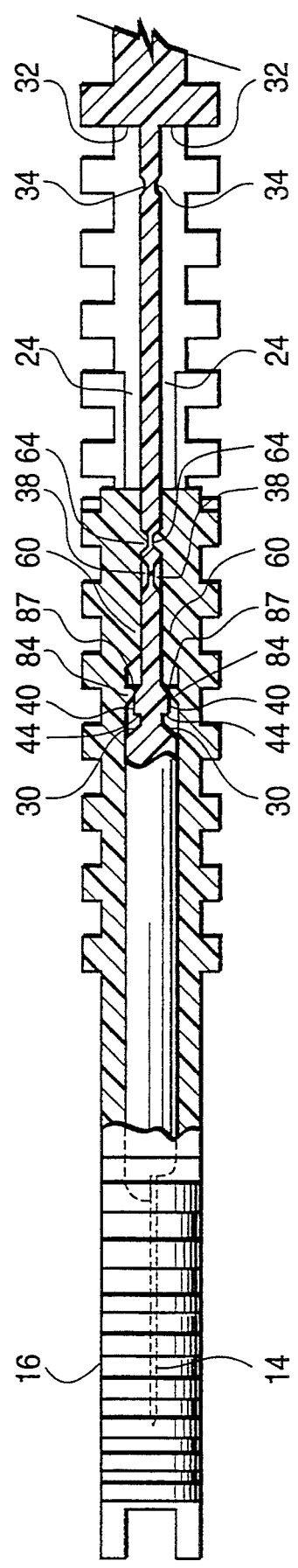
FIG. 7 is a cross-sectional view of a first embodiment of the scalpel of the present invention taken generally on line C—C of FIG. 1, wherein the guard is in the temporary protective position.
Figure 8:
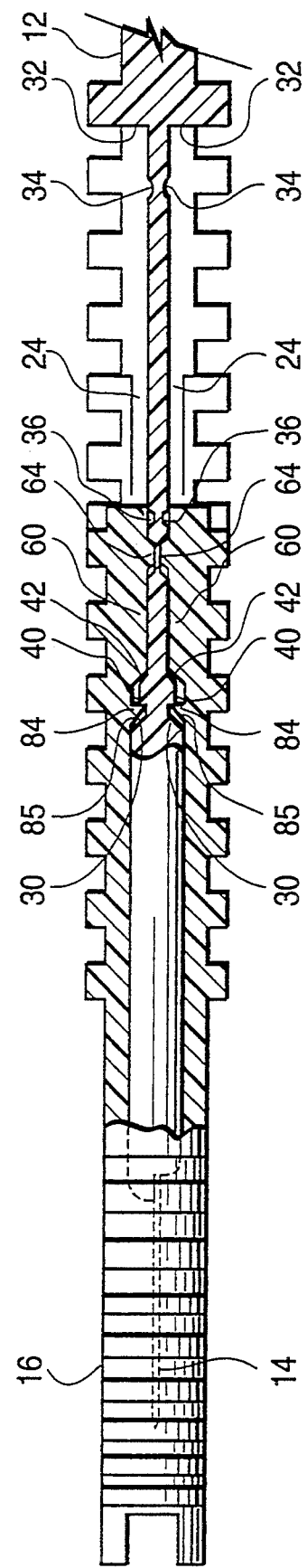
FIG. 8 is a cross-sectional view of a first embodiment of the scalpel of the present invention taken generally on line C—C of FIG. 1, wherein the guard is in the permanently protective position.

Referring now to FIG. 1, a scalpel constructed in accordance with the present invention is illustrated and generally designated 10. Scalpel 10 includes a handle 12, a blade 14 and a guard 16. Preferably, the blade 14 is permanently secured at one end of handle 12, for example, by staking. However, various sizes of blades 14 may be permanently or releasably attached to handle 12, depending on the nature of the use of the scalpel 10. The handle 12, which comprises an upper surface or edge 18 and a lower surface or edge 20, and a first side and second opposite side (not shown), preferably is formed entirely of a plastic material. The handle 12 also comprises an engaging surface 22 (shown in FIG. 2), for example, a channel, which is located proximate the blade end of the handle 12. As discussed below, the guard 16 is movably mounted within the engaging surface 22 (shown in FIG. 2) of the handle 12, such that the guard 16 is movable along the length of the engaging surface between a plurality of positions including a retracted position exposing the blade 14 for use as illustrated in FIG. 1, a temporary protective position covering and overlying the blade 14 as illustrated in FIG. 7 and a permanently locked position covering the blade 14 as illustrated in FIG. 8.

Figure 2:
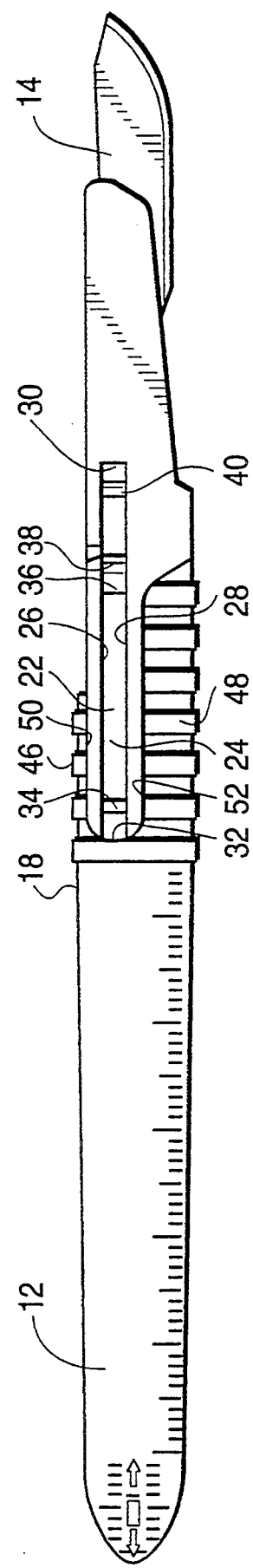
FIG. 2 is a side plan view of a first embodiment of the handle of the present invention, without the attaching guard.

Turning to FIG. 2, a side plan view of a first embodiment of the handle 12 of the present invention is shown, without the attaching guard 16. As shown in FIG. 2, the handle 12 comprises an engaging surface 22 which is located proximate the blade end of the handle 12. The guard 16 (not shown) contacts the engaging surface 22, wherein the engaging surface 22 in conjunction with the guard 16 secures the guard 16 to the handle 12 and allows the guard 16 to move along the length of the engaging surface 22. In the embodiment of the invention shown in FIG. 2, the engaging surface 22 comprises a channel, hereinafter referred to as a keyway 22.

The keyway 22 is formed by substantially similar grooves 24 (only one is shown) on each side of the handle 12 at the same location and each groove 24 is defined by upper and lower ledges 26,28 and forward and rearward edges 30,32 which function as forward and rearward stops, respectively. Preferably, the grooves 24 begin and end at the same location on each side of the handle 12, are parallel to one another, and are located at the same vertical position on each side of the handle 12. The keyway 22 preferably is parallel to the longitudinal axis of the handle 12. For the purpose of clarity, the keyway 22 is said to have a forward portion, which is defined as the half of the keyway 22 closest to the end of the handle 12 securing the blade 14 and a rearward portion, which is the defined as the half of the keyway 22 farthest from the blade end.

Furthermore, each groove 24 of the keyway 22 comprises a first detent 34, for example, a notch or an opening, located in the rearward portion of the keyway 22 and a second detent 36 and third detent 38 located in the forward portion of the keyway 22. The detents 34,36,38 function to releasably maintain the movable guard 16 in the various positions. The keyway 22 also comprises two latch wedges 40, each having an angled end 42 and a locking end 44. One latch wedge 40 is disposed in each groove 24 between the third detent 38 and the forward edge 30 of the groove 24. Each latch wedge 40 is formed such that the locking end 44 faces the forward edge 30 and the angled end 42 faces the rearward edge 32. Preferably, the locking end 44 of each latch wedge 40 is perpendicular to both the longitudinal and vertical axis of the keyway 22.

The handle 12 also comprises a plurality of ribs 46 longitudinally spaced one from the other along the forward portion of the upper edge 18 of the handle 12. Similar ribs 48 are disposed along the lower edge 20 and the sides of the handle 12. The ribs 46,48 facilitate gripping the scalpel 10 by the surgeon during use and are exposed in all positions of the scalpel's guard 16. Furthermore, the handle 12 forms a receiving cavity for a portion of the guard 16, wherein the receiving cavity contributes to the prevention of pivotal movement of the guard 16 relative to the handle 12.

More specifically, the width of the handle 12 surrounding the keyway 22 is reduced so as to define an upper surface 50 of the receiving cavity and a lower surface 52 of the receiving cavity, on each side of the handle 12. As discussed hereinafter, the receiving cavity formed by the handle 12 provides additional means of securing the guard 16 to the handle 12 so that the guard 16 and the handle 12 operate as an unit with the guard 16 in the retracted position. Also provided along one and preferably both side faces of the handle 12, is dimensional indicia, for example, centimeters, as shown in FIG. 2.

Figure 4:
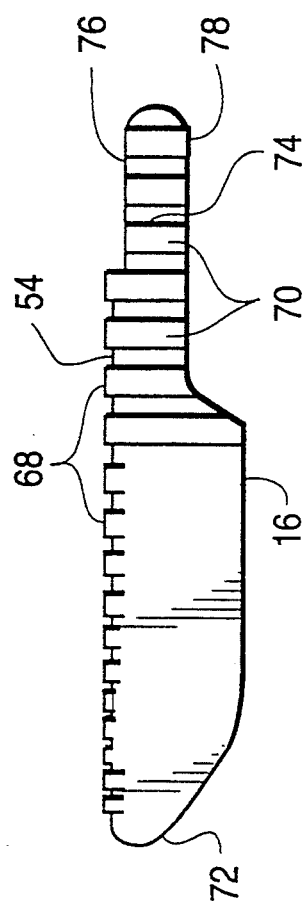
FIG. 4 is a side plan view of the guard shown in FIG. 3.
Figure 3:
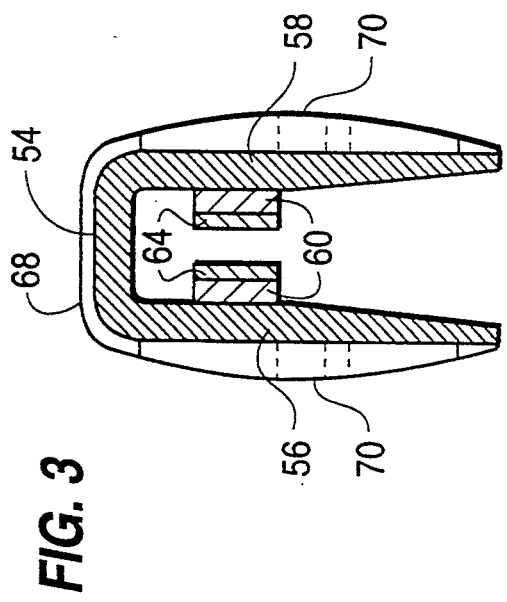
FIG. 3 is a cross-sectional view of a first embodiment of the guard of the present invention taken generally on line A—A of FIG. 1.
Figure 5:
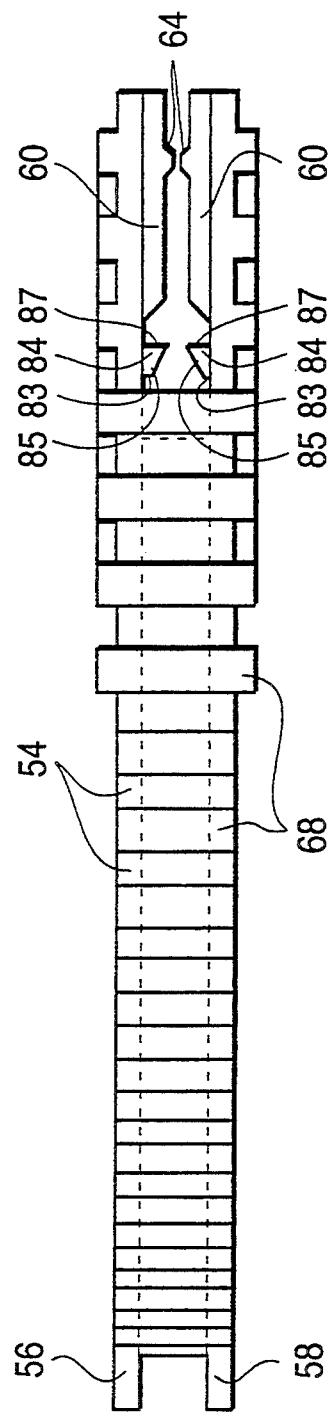
FIG. 5 is a top plan view of a first embodiment of the guard of the present invention.

FIGS. 3–5 illustrate the guard 16 of the present invention. More specifically, FIG. 3 is a cross-sectional view of a first embodiment of the guard 16 of the present invention taken on line A—A of FIG. 1. As shown in FIG. 3, the guard 16 is preferably integrally molded of one piece of plastic so as to form a U-shaped channel comprising an upper surface 54 and elongated side members 56, 58 which extend downwardly from the upper surface 54. Each side member 56, 58 comprises an inwardly extending flange or key 60 which functions to movably mount the guard 16 to the handle 12. Each key 60 is elongated in shape and has a height (i.e., breadth measured perpendicular to the longitudinal axis of the handle 12) such that when the key 60 is positioned in the groove 24 of the keyway 22, the key 60 engages the upper and lower ledges 26, 28 of the keyway 22. Furthermore, a latching detent 64 is disposed on each key 60. The latching detents 64 engage with the detents 34,36,38 disposed in the keyway 22 so as to releasably maintain the guard 16 in various positions along the keyway 22. The two side members 56,58 preferably are mirror images of one another.

Furthermore, as illustrated best in FIG. 4, the guard 16 also comprises a plurality of ribs 68 longitudinally spaced one from the other along the upper surface 54 of the guard 16. Similar ribs 70 are disposed along the rear portion of each side member 56,58. In the preferred embodiment of the invention, as shown in FIG. 1, the ribs 46,48 on the handle 12 align vertically with the ribs 68,70 on the guard 16, when the guard 16 is in the retracted position. As previously stated, the ribs 46,48,68,70 facilitate gripping the scalpel 10 by the surgeon during use. However, the ribs 68 on the guard 16 also provide a frictional contact surface readily and easily gripped by a digit of the same hand holding the scalpel for sliding the guard 16 between and into its various positions along the handle 12.

As shown in FIG. 4, which is a side plan view of the guard 16 shown in FIG. 3, each side member 56,58 comprises an elongated side having a forward end 72, for example an arcuately shaped end, and a guide arm 74 formed on the rear end. Each guide arm 74 (only one is shown) is parallel to the longitudinal axis of the elongated side and is free from attachment with the top surface 54 of the guard 16. As a result, each guide arm 74 comprises an upper edge 76 and lower edge 78. Also, each guide arm 74 is formed so that the height of the guide arm 74 (i.e., breadth of the guide arm 74 measured perpendicular to the longitudinal axis of the handle 12) is such that when the guard 16 is in the retracted position, the upper edge 76 and the lower edge 78 of each guide arm 74 are sufficiently close to the upper and lower surfaces 50, 52 of the receiving cavity formed by the handle 12. The receiving cavity functions to prevent pivotal movement of the guard 16 relative to the handle 12 when the guard 16 is in the retracted position.

FIG. 5 depicts a top plan view of the guard 16 of the first embodiment of the present invention. As shown in FIG. 5, the inwardly extending key 60 is formed on each side member 56,58 on the rear end of the guide arm 74 of each side member 56,58. The length of the key 60 (i.e., breadth measured parallel to the longitudinal axis of the handle 12) preferably is greater than the height of the keyway 22. It is significant that each key 60 engage the upper and lower ledges 26, 28 of the keyway 22 and that each key 60 is elongated in the keyway 22 so that any torquing action on the guard 16 tending to pivot the forward end of the guard 16 away from the blade 14 is forcefully resisted by the engagement of the key 60 with the upper and lower ledges 26,28 of the keyway 22.

An inwardly extending latching detent 64 is formed on the key 60 on each guide arm 74. The latching detent 64 disposed on each key 60 engages with the detents 34,36,38 formed in the keyway 22 so as to releasably maintain the guard 16 in either the retracted position or the temporary protective position. Furthermore, each guide arm 74 comprises an inwardly extending latch 84 located forward of the key 60. Each latch 84 comprises a generally triangular ramp having an angled end 85 and a locking end 87. Preferably, similar to the latch wedges 40 disposed in the keyway 22, the locking end 87 is perpendicular to both the longitudinal and vertical axis of the keyway 22. The lower portion 83 of the angled end 85 of each latch 84 is also perpendicular to both the longitudinal and vertical axis of the keyway 22. The lower portion 83 of the angled end 85 of each latch 84 provides a positive stop when engaging the forward edge 30,32 of each groove 24 of the keyway 22. Further, the lower portion 83 is sufficiently minimal so as to not prevent the latch 84 from passing over the latch wedge 40. The function of the positive stop is to prevent outward movement of the guide arms 74 upon positioning the guard 16 in the permanently protected position. The angled end 85 of the latch 84 faces the angled end 42 of the latch wedge 40 when the guard 16 is in the retracted or temporary protective position.

To assemble the guard 16 and the handle 12 to one another, the guide arms 74 of the side members 56, 58 are spread apart such that the key 60 and the latch 84 on the guide arm 74 on one side member 56, are received in the groove 24 on one side of the handle 12, while the key 60 and the latch 84 on the guide arm 74 on the other side member 58 are received in the groove 24 on the other side of the handle 12. However, because of the resiliency of the guard 16, the guide arms 74 return to their original position, wherein the keys 60 on the guide arms 74 are positioned within the keyway 22 on the respective sides of the handle 12. The engagement between the keys 60 and the grooves 24 of the keyway 22 prevent the guard 16 from separating from the handle 12. However, the keys 60 are movable along the length of the keyway 22. As a result, the guard 16 is mounted for longitudinal sliding movement relative to the handle 12. It will be appreciated that the engagement between each guide arm 74 and the handle 12 can be reversed, wherein the key 60 is mounted on the handle 12 and the keyway 22 is formed on the guide arm 74.

Figure 6:
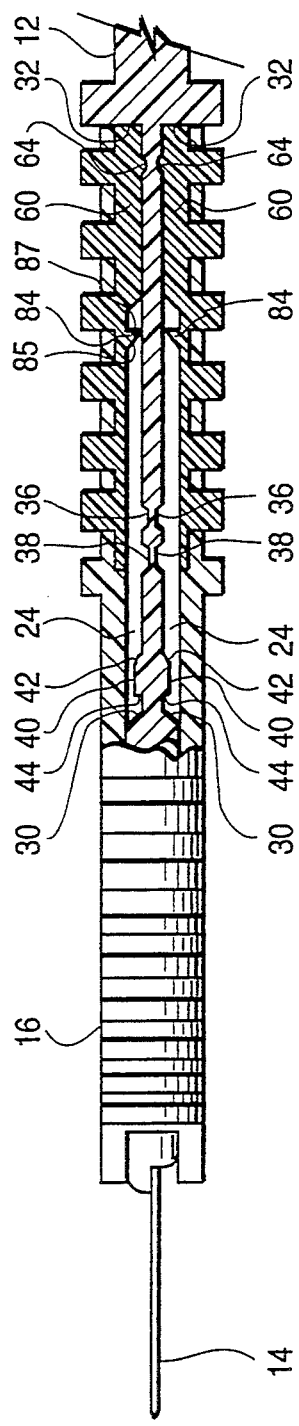
FIG. 6 is a cross-sectional view of a first embodiment of the scalpel of the present invention taken generally on line C—C of FIG. 1, wherein the guard is in the retracted position.

Referring now to the embodiment hereof illustrated in FIGS. 6-8, which are cross-sectional views of the preferred embodiment of the present invention taken along line C—C of FIG. 1, the guard 16 of the scalpel 10 is depicted in a retracted position exposing the blade 14 for use in FIG. 6, a temporary protective position covering the blade 14 in FIG. 7 and a permanently locked position covering the blade 14 in FIG. 8. Permanent locking position means a position of the guard 16 relative to the handle 12 where the guard 16 cannot be retracted or displaced from its permanent locked position without destroying either the guard 16, handle 12 or both.

Turning to FIG. 6, the guard 16 is shown fully retracted exposing the blade 14 for use. As shown in FIG. 6, in the retracted position the rear end of each side member 56,58 of the guard 16 (i.e., guide arm 74) engages the rearward edges 32 of the grooves 24 forming the keyway 22. Furthermore, the latching detents 64 on the keys 60 of the guard 16 engage with the first detent 34 formed in each groove 24. The resiliency of the guard 16 forces the engagement between the latching detents 64 on the key 60 and the first detents 34 on the keyway 22, thereby maintaining the guard 16 in the retracted position.

The resilient nature of the guide arms 74 of the guard 16 enables the guard 16 to be detented in its retracted position yet allows the sliding movement of the guard 16 to the temporary protective position shown in FIG. 7. More specifically, to move the guard 16 to the temporary protective position, the latching detents 64 on each guide arm 74 of the guard 16 are biased outwardly away from one another and are removed from the first detent 34 of the keyway 22. Each key 60 on the guard 16 travels forward in the corresponding groove 24 of the keyway 22 until the latching detents 64 disposed on each key 60 are adjacent the second detents 36 in the keyway 22, wherein the resilient nature of the guard 16 forces the latching detents 64 on each key 60 into engagement with the second detents 36 thereby securing the guard 16 in a second position. The position of the second detent 36 in each groove 24 of the keyway 22 is selected such that upon engagement with the latching detents 64 of the guard 16, the guard 16 is completely covering the blade 14, as shown in FIG. 7.

As shown in FIG. 1, it will be appreciated that by holding the handle 12 in the palm of the individuals hand and placing a digit of the same hand on the ribs 68 disposed on the upper surface 54 of the guard 16, the guard 16 may be advanced from the retracted position to the temporary protective position and vice versa, as required. As previously stated, the latching detent 64 on the key 60 on each guide arm 74 is resiliently displaced so as to enable each key 60 to pass along the groove 24 between the various positions. It is significant that the guard 16 may be disposed in either direction with only one hand, thereby freeing the other hand for work.

After use and when it is desirable to dispose of the scalpel 10, the guard 16 may be advanced into the permanently locked position illustrated in FIG. 8. To locate the guard 16 in the permanent locked position covering the blade 14, the guard 16 is displaced forwardly from the position illustrated in FIG. 7 to the position illustrated in FIG. 8. In displacing the guard 16 forwardly, similar to moving the guard 16 from the retracted position to the temporary protective position, the latching detent 64 on each side member 56, 58 of the guard 16 is biased outwardly away from one another and is removed from the second detent 36 on each groove 24 of the keyway 22. As the guard 16 is displaced forward, the angled end 85 of the latch 84 on each guide arm 74 engages the angled end 42 of the latch wedge 40 on each groove 24, and the latch 84 completely rides over the latch wedge 40 such that the locking end 44 of the latch wedge 40 and the locking end 87 of the latch 84 face one another. Specifically, upon the latch 84 engaging the latch wedge 40, the latch 84 resiliently bears against the latch wedge 40. As the latch 84 traverses the latch wedge 40, the latch 84 and consequently the guide arms 74, are displaced outwardly so as to allow the latch 84 to pass over the latch wedge 40. Upon passing over the latch wedge 40, the latch 84 is again forced by the resilient nature of the guard 16 into engagement with the keyway 22.

Figure 9:
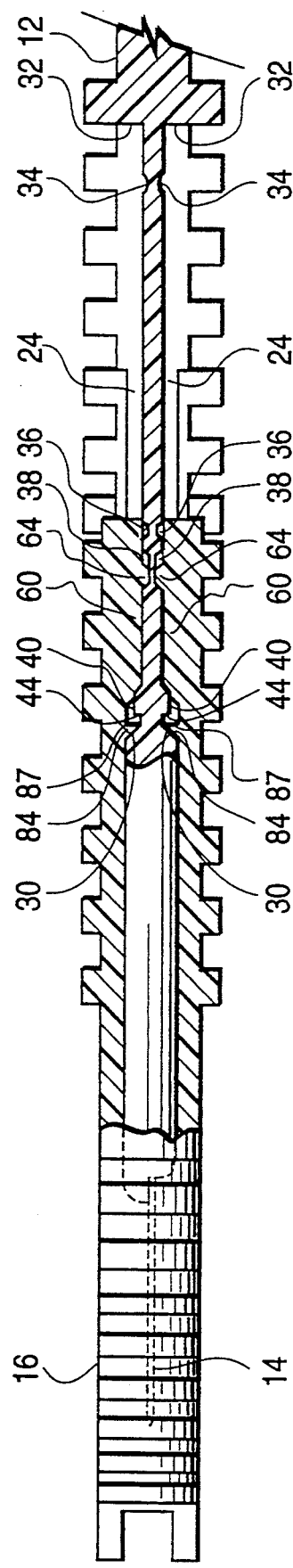
FIG. 9 is a cross-sectional view of a first embodiment of the scalpel of the present invention taken generally on line C—C of FIG. 1, wherein the guard is in the most forward position relative to the handle.

Once the latch 84 is completely forward of the latch wedge 40, the latching detent 64 on each side member 56,58 of the guard 16 engage the third detent 38 in the corresponding groove 24 of the keyway 22 so as to stabilize the guard 16 in a permanently locked position. Rearward movement of the guard 16 relative to the handle 12 is prevented in this permanently locked position by the engagement of the locking end 87 of the latch 84 against the locking end 44 of the latch wedge 40, which are preferably parallel to one another and therefore cannot be biased out of the path of one another as is shown in FIG. 8. Further forwardly movement of the guard 16 is prevented by the engagement of the latch 84 with the forward edge 30 of the grooves 24 as is shown in FIG. 9. Thus, the guard 16 is permanently secured in a position covering the blade 14.

It will be appreciated that throughout the full range of sliding movement of the guard 16 relative to the handle 12, the resiliency of the guard 16 functions to prevent the side members 56,58 of the guard 16 from spreading laterally outward away from the handle 12.

Figure 10:
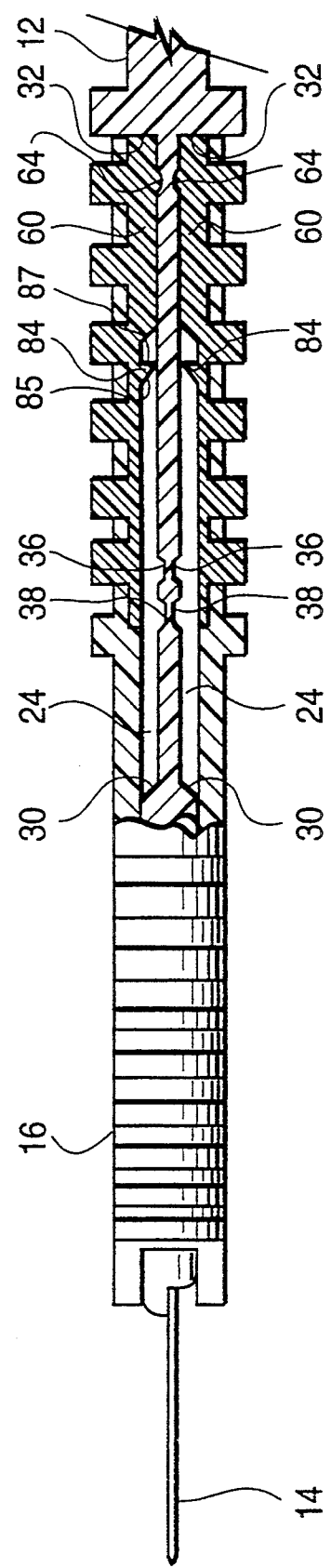
FIG. 10 is a cross-sectional view of a second embodiment of the scalpel handle of the present invention.

In a second embodiment of the present invention, as shown in FIG. 10, the latch wedge 40, which is disposed on the forward portion of each keyway 22 in the first embodiment, is removed from each keyway 22. As a result, the guard 16 is movably between the temporary protective position covering the blade 14 and the retracted position exposing the blade 14. However, without the latch wedge 40 in the keyway 22, the guard 16 cannot be located in the permanent protective position.

FIGS. 11-16 illustrate a third embodiment of the present invention, which is identical to the first and second embodiments except for the additional elements noted hereafter. As explained in detail below, the guard 16 further comprises a spring element 90 and a retaining latch 92 which operate in conjunction with a stepped surface 94 and a retaining wedge 96 formed on the handle 12 to maintain the guard 16 in the temporary protective position unless a force substantially perpendicular to the axis of motion of the guard is exerted on the guard 16. As a result, an inadvertent force applied to the guard 16 does not result in the unwanted retraction of the guard.

Figure 12:
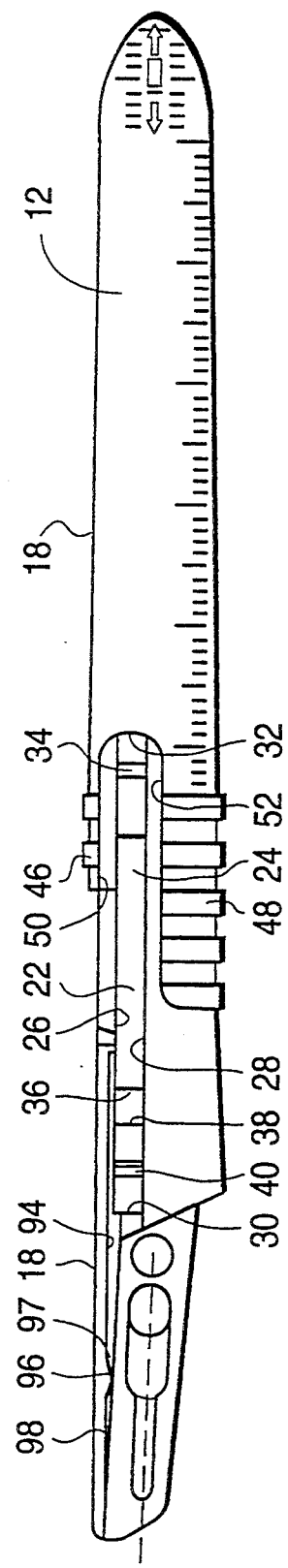
FIG. 12 is a side plan view of a third embodiment of the handle of the present invention.

Referring to FIG. 12, which illustrates a side view of the handle 12 of the third embodiment of the present invention, the stepped surface 94 is formed on one side of the handle 12, and is located along the forward portion of the handle 12. The stepped surface 94 is formed by reducing the width of the handle 12 on one side thereof below the upper surface 18 of the handle 12. Preferably, the stepped surface 94 and the upper surface 18 of the handle 12 are substantially parallel to one another.

Figure 13:
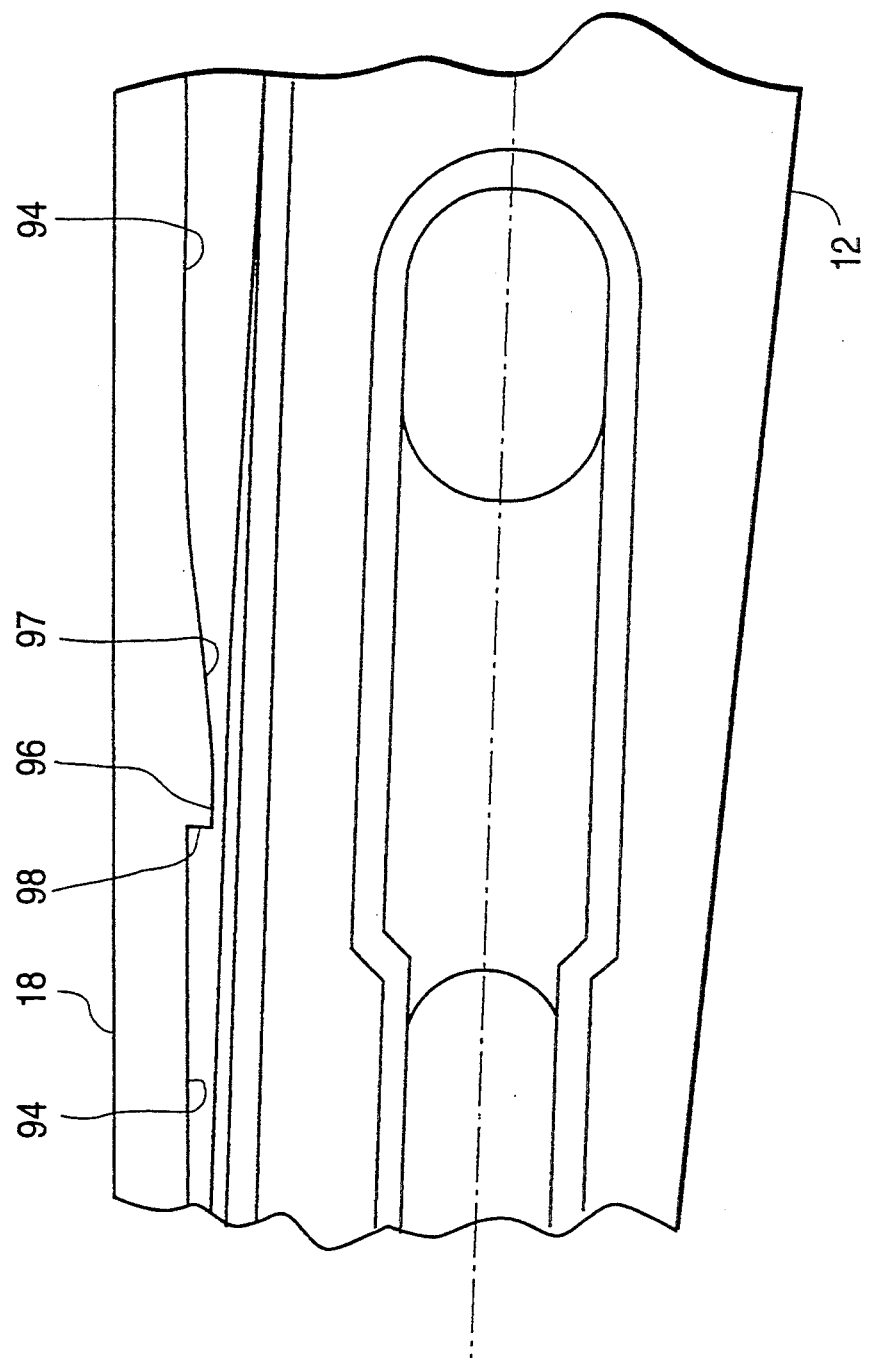
FIG. 13 is an enlarged view of a portion of the handle illustrated in FIG. 12.

The retaining wedge 96 is disposed on the stepped surface 94 and extends downwardly away from the upper surface 18 of the handle 12. The retaining wedge 96, which is generally triangular in shape, comprises an angled end 97 and a locking end 98, and is positioned such that locking end 98 extends perpendicularly downward from the stepped surface 94. The locking end 98 is closer to the forward portion of the scalpel than the angled end 97. FIG. 13 is an enlarged view of the portion of the handle 12 comprising the stepped surface 94 and the retaining wedge 96.

Figure 15:
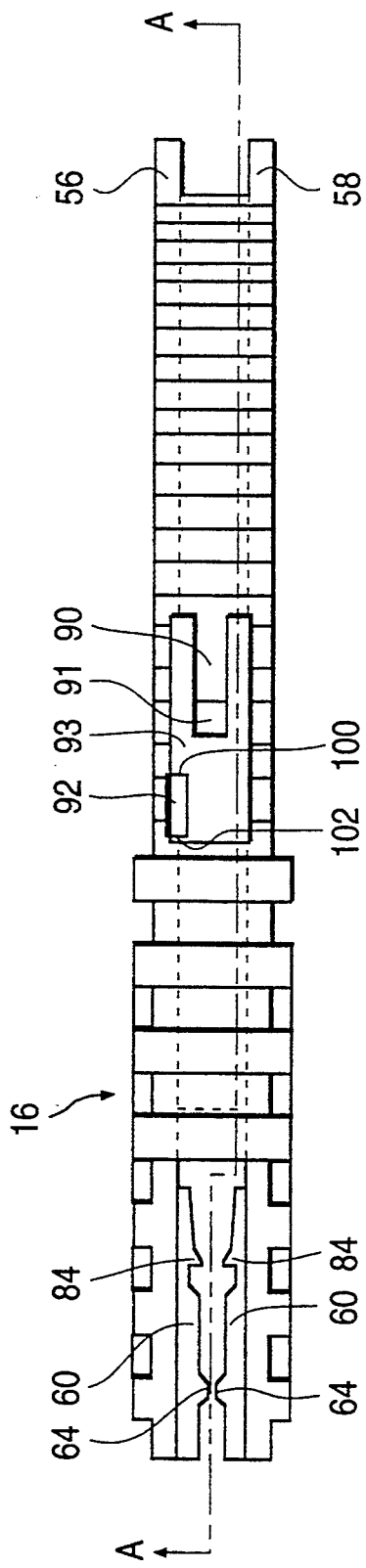
FIG. 15 is a top plan view of the guard illustrated in FIG. 14.
Figure 14:
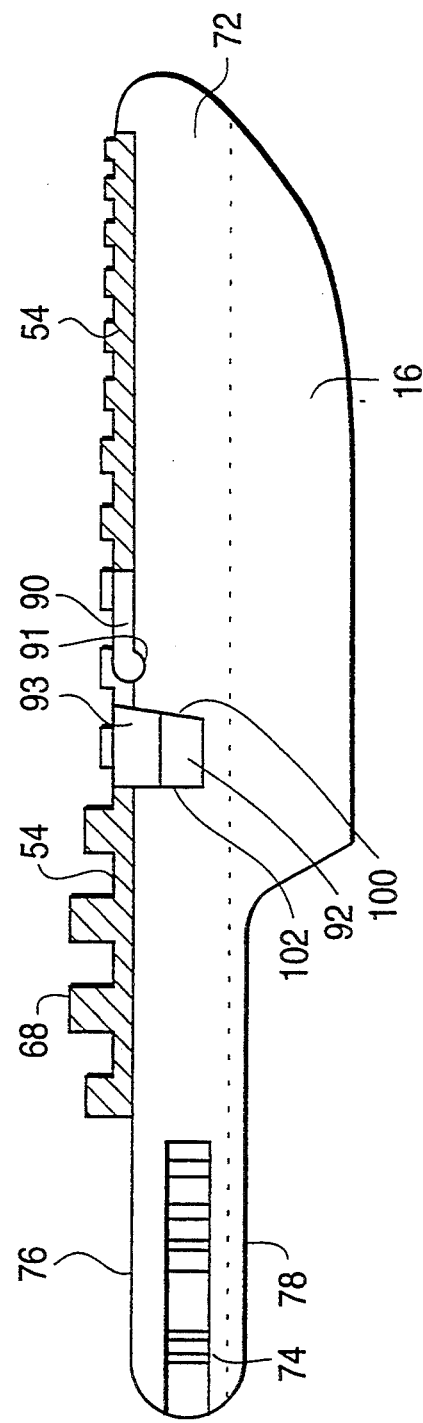
FIG. 14 is a cross-sectional view of a third embodiment of the guard of the present invention taken generally on line A—A of FIG. 15.
Figure 16:
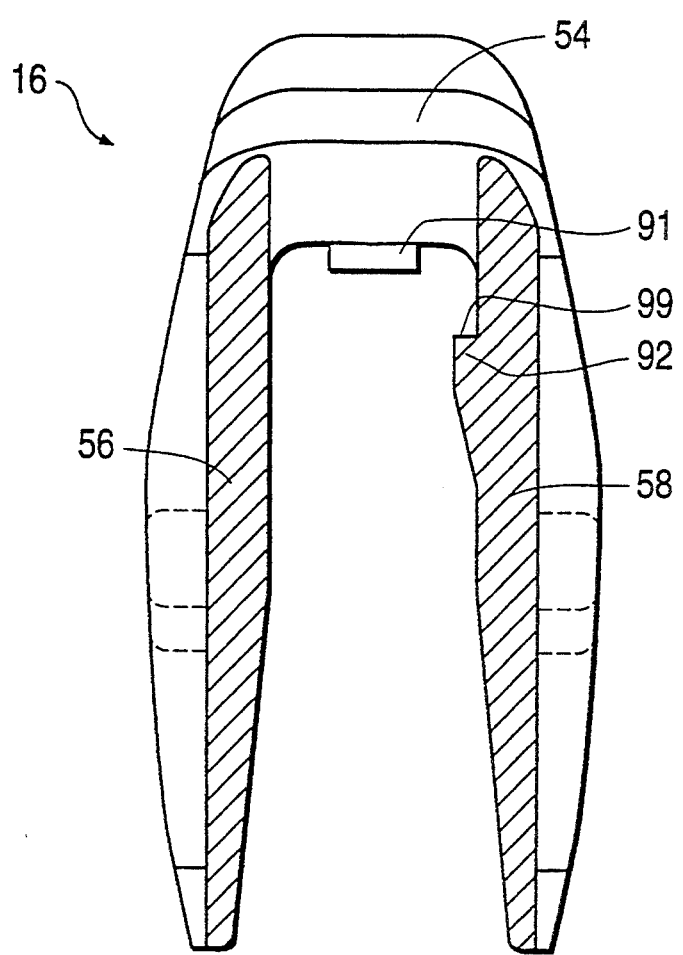
FIG. 16 is a cross-sectional view of the guard of the third embodiment of the present invention.

The guard of the third embodiment of the present invention is illustrated in FIGS. 14-16. Referring to FIGS. 14 and 15, the spring element 90 of the guard, which is resilient in nature, extends into an opening 93 formed in the upper surface of the guard 16. The free end 91 of the spring element 90 exhibits an increased thickness such that a portion thereof extends into the U-shaped channel formed by the guard 16. As a result, when the guard 16 is mounted to the handle 12, the free end 91 of the spring element 90 engages the upper surface 18 of the handle 12 and exerts a downward force on the handle 12. This downward force urges the separation of the forward portion of the guard 16 and the upper surface 18 of the handle 12.

However, referring to FIG. 16, the guard 16 also comprises a retaining latch 92 disposed on the inner surface of one of the side members 56,58. The retaining latch 92 has a substantially rectangular shape with side walls 100, 102 and an upper surface 99 which extends perpendicularly into the U-shaped channel. The retaining latch 92 is disposed on the side member that is adjacent the side of the handle 12 comprising the stepped surface 94 when the guard 16 is mounted to the handle 12.

Further, the retaining latch 92 is positioned on the side member such that when the guard 16 is mounted to the handle 12, the upper surface 99 of the retaining latch 92 and the stepped surface 94 of the handle 12 are substantially parallel to one another. The upper surface 99 of the retaining latch 92 is positioned just beneath the stepped surface 94 of the handle 12.

Once the guard 16 is mounted to the handle 12, the retaining latch 92 and the stepped surface 94 prevent the forward portion of the guard 16 and the handle 12 from separating beyond the pre-designed limits. If an upward force is exerted on the guard 16, the upper surface 99 of the retaining latch 92 engages the stepped surface 94 of the handle 12. The stepped surface 94 operates as an upward stop preventing further upward movement of the guard 16.

As stated above, the third embodiment of the present invention provides enhanced safety in that the guard 16 cannot be retracted without first exerting a downward force on the guard. Further, as the spring element 90 constantly exerts a downward force on the handle 12, all vertical play between the guard 16 and the handle 12 is eliminated, and overall stability of the guard 16 is further enhanced. The operation of the third embodiment of the safety scalpel is described below.

The third embodiment of the guard 16 is mounted to the handle 12 in the same manner as disclosed in the first two embodiments. The resilient nature of the guard 16 allows the retaining latch 92 to pass over the upper surface 18 of the handle 12 and thereafter forces the retaining latch 92 into the normal position as explained above. Once mounted, the spring element 90 exerts a downward force on the upper surface 18 of the handle 12 such that the upper surface 99 of the retaining latch 92 engages the stepped surface 94 of the handle 12.

As the guard 16 is transitioned from the retracted position to the temporary protective position, the upper surface 99 of the retaining latch 92 slides along the stepped surface 94 of the handle 12. Eventually, the retaining latch 92 engages the angled end 97 of the retaining wedge 96 disposed on the stepped surface 94. As the forward movement of the guard 16 continues, the retaining latch 92 is forced in the downward direction (i.e. the spring element 90 is compressed) until the retaining latch 92 is completely forward of the retaining wedge 96.

At this point, the spring element 90 forces the guard 16 in the upward direction such that the rear side wall 102 of the retaining latch 92 abuts the locking end 98 of the retaining wedge 96. As a result, the locking end 98 operates as rearward stop which prevents rearward movement of the guard 16 if the force attempting to move the guard 16 is applied substantially parallel to the longitudinal axis of the handle 12.

The retaining wedge 96 and retaining latch 92 are positioned on the handle 12 and guard 16, respectively, such that when the retaining latch 92 is located in front of the retaining wedge 96 the blade is completely covered, and as discussed above with regard to the first and second embodiments, the latching detents 64 disposed on each key 60 are adjacent the second detents 36 in the keyway 22.

In order to transition the guard 16 from the temporary protective position to the retracted position, a substantially downward force must be exerted on the upper surface of the guard 16. The force must be sufficient to compress the spring element 90 such that the rear side wall 102 of the retaining latch 92 is positioned below the locking end 98 of the retaining wedge 96. Once this occurs, the guard 16 can then be retracted by applying a rearward force which is substantially parallel to the longitudinal axis of the handle 12. As with prior embodiments, the guard 16 may be positioned in either the temporary protective position or the retracted position, as required, and with the use of a single hand.

The operation of the safety scalpel of the third embodiment is the same as the first and second embodiments in both the retracted and the permanently locked positions.

Variations of the embodiments of the present invention are possible. For example, the engagement between the guide arm 74 and the handle 12 can be reversed. More specifically, the outwardly extending key 60 can be disposed on the handle 12, and the groove 24 which receives the key 60 can be formed on the guide arm 74 of the guard 16. The resiliency of the guard 16 in conjunction with the engagement between the key 60 and the groove 24 prevent the removal of the guard 16 from the handle 12 while allowing for the longitudinal movement of the guard 16 relative to the handle 12 in the same manner as the first and second embodiments.

In another variation, additional detents are disposed along the keyway 22 so that the guard 16 can be releasably maintained at various positions which correspond to various degrees of blade exposure.

In another variation, the width of a portion of the upper edge 18 of the handle 12 above the forward portion of the keyway 22 is reduced so as to minimize the distance the guide arms 74 must be separated from one another during the mounting of the guard 16 to the handle 12.

In another variation, the angled end 85 of the latch 84 on the guide arms 74 forms a right triangle with the surface of the keyway 22 and the locking end 87 of the latch 84.

In yet another variation, the latch wedge 40, which functions to permanently secure the guard 16 in the protective position, is disposed in only one of the grooves 24 of the keyway 22.

In yet another variation, the stepped surface 94, retaining wedge 96 and retaining latch 94 can be formed on both sides of the handle 12 and guard 16, respectively, in accordance with the third embodiment of the present invention.

Figure 17:
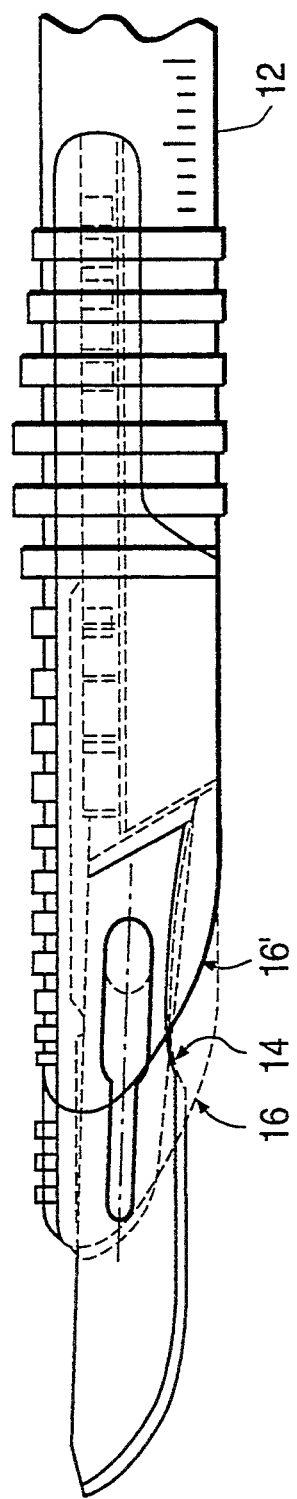
FIG. 17 is a side view of the scalpel of the present invention illustrating that the maximum distance the guard can be varied so as to provide alternate blade exposures.

In yet another variation, the distance the guard travels in the rearward direction can be varied so as to allow for greater exposure of the blade, as indicated by guard 16 and 16' in FIG. 17. This can be accomplished, for example, by extending the keyway 22 in the rearward direction, and adjusting the position of the detents and latches accordingly. As a result, it is possible to retract the blade sufficiently such that the inventive scalpel is functionally equivalent to a non-guarded scalpel.

Figure 11:
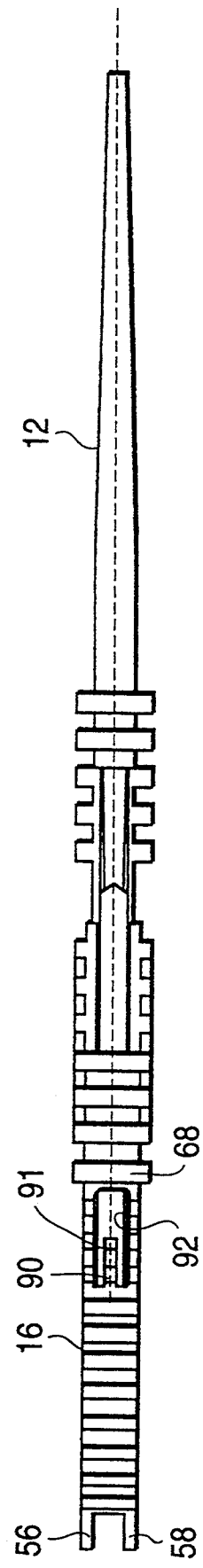
FIG. 11 is a top plan view of a third embodiment of the disposable scalpel of the present invention illustrating the guard in the extended position covering the blade.

In yet another variation, as shown in FIG. 11, the height of the ribs on the upper surface of the guard vary so as to form an arcuate shape so as to facilitate the user's operation of the guard.

The embodiments described above provide a number of significant advantages. Because the guard 16 is secured to the handle 12 by the resiliency of the guard 16 in combination with the groove 24 on the handle 12 and the key 60 on the guard 16, no additional material or parts are required to assemble the guard 16 to the handle 12.

As yet another advantage, a surface of the handle 12 of the scalpel is fully exposed in all positions of the guard 16 so that control of the cutting edge by the surgeon may be maintained by direct finger contact with the scalpel handle 12 during use. Moreover, the guard 16 is slidable along the handle 12 between all positions using only one hand. It does not require two hands to move the guard 16 between its protective and retracted positions. Further, the guard 16 is slidable between retracted and temporary protective positions multiple times, whereby the scalpel 10 may be used, set aside with the guard 16 in its temporary protective position, and then reused with the guard 16 movable again into its retracted position. Still further, the construction of the handle 12 and guard 16 may be of all plastic material whereby the scalpel 10 may be formed and assembled inexpensively.

As another advantage, in all of the embodiments hereof, it will be appreciated that the connection between the guard and handle provides a scalpel assembly of greater integrity and strength, i.e., stiffer, than either of the handle or guard individually.

As yet another advantage, the guard may be formed of a transparent or semi-transparent material. Thus, with appropriate identification markings on the blade, the type of blade can be identified by the user with the guard in its protective position overlying the blade and without the need to retract the guard. Alternatively, the guard may be opaque and have a window with or without a magnifying glass and through which window the type of blade may be identified. Various types of coated blades or edges, e.g., blades or edges coated with polymer materials, such as polytetrafluoroethylene, may be used and the invention hereof is not limited to any particular blade, coated or uncoated.

In one embodiment, a force substantially perpendicular to the axis of motion of the guard must be applied to the guard in order to release it from the temporary protective position, thereby eliminating the possibility of the guard inadvertently retracting in response to a force striking the tip of the guard.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A scalpel comprising:
    a handle comprising exposed surfaces so as to facilitate gripping the handle during use;
    a blade carried by said handle proximate to one end thereof;
    a guard movably mounted to said handle for sliding movement relative to said handle between a protective position covering said blade and a retracted position exposing said blade for use; and
    a lock for releasably securing said guard to said handle in the retracted position and in the protective position, said lock requiring a force substantially perpendicularly to the axis of motion of said guard to disengage said guard from said protective position;
    said lock comprising a stepped surface and a retaining wedge disposed on said handle, wherein said stepped surface is substantially parallel to an upper surface of said handle, and said retaining wedge is disposed surface; and said lock further comprising a retaining latch disposed on a side member of said guard, said retaining latch having an upper surface substantially parallel to said stepped surface.

2. A scalpel according to claim 1 wherein said guard further comprises a spring element disposed on a surface of said guard such that said spring element exerts a downward force on said upper surface of said handle.

3. A scalpel according to claim 2 wherein said spring element forces the engagement of said retaining wedge and said retaining latch so as to secure said guard in said protective position.

4. A scalpel according to claim 3, wherein a force substantially parallel to the axis of motion of said guard is applied to said guard to disengage said retaining wedge and said retaining latch so as to allow the transition of said guard from the protective position to the retracted position.

5. A scalpel according to claim 2 wherein said spring element forces the engagement of said stepped surface and said retaining latch, wherein said stepped surface operates as an upward stop so as to limit the movement of said guard in the upward direction.

6. A scalpel according to claim 1 wherein said guard is integrally molded of one piece of plastic so as to form a U-shaped channel, wherein side members extend downwardly from an upper surface.

7. A scalpel according to claim 6 wherein said side members of said guard are resilient such that the resiliency of said side members of said guard forces said side members inwardly so as to maintain engagement between said engaging surface and said side members of said guard.

8. A scalpel according to claim 7 wherein said guard further comprises a plurality of ribs longitudinally spaced one from the other disposed along said upper surface and said side members so as to facilitate gripping the handle during use.

9. A scalpel according to claim 1 wherein said engaging surface on said handle is located on said handle such that a sufficient portion of the handle remains substantially completely exposed with the guard in the retracted position so as to allow the operator to secure the handle in one hand while shifting the position of the guard a digit of the same hand.

10. A scalpel comprising:
a handle comprising exposed surfaces so as to facilitate gripping the handle during use;
a blade carried by said handle proximate to one end thereof;
a guard movably mounted to said handle for sliding movement relative to said handle between a retracted position exposing said blade for use, a temporary protective position covering said blade, and a permanently locked position covering the blade; and
a lock for releasably securing said guard to said handle in the retracted position and in the protective position and for permanently securing the guard in the permanently locked position, said lock requiring a force substantially perpendicularly to the axis of motion of said guard to disengage said guard from said temporary protective position and transition said guard to the retracted position;
said lock comprising a stepped surface and a retaining wedge disposed on said handle, wherein said stepped surface is substantially parallel to an upper surface of said handle, and said retaining wedge is disposed on said stepped surface; and said lock further comprising a retaining latch disposed on a side member of said guard, said retaining latch having an upper surface substantially parallel to said stepped surface.

11. A scalpel according to claim 10 wherein said guard further comprises a spring element disposed on the surface of said guard such that said spring element exerts a downward force on said upper surface of said handle.

12. A scalpel according to claim 11 wherein said spring element forces the engagement of said retaining wedge and said retaining latch so as to secure said guard in said temporary protective position.

13. A scalpel according to claim 12, wherein a force substantially parallel to the axis of motion of said guard is applied to said guard to disengage said retaining wedge and said retaining latch so as to allow the transition of said guard from the temporary protective position to the retracted position.

14. A scalpel according to claim 11 wherein said spring element forces the engagement of said stepped surface and said retaining latch, wherein said stepped surface operates as an upward stop so as to limit the movement of said guard in the upward direction.

15. A scalpel according to claim 10 wherein said guard is integrally molded of one piece of plastic so as to form a U-shaped channel, wherein side members extend downwardly from an upper surface.

16. A scalpel according to claim 15 wherein said side members of said guard are resilient such that the resiliency of said side members of said guard forces said side members inwardly so as to maintain engagement between said engaging surface and said side members of said guard.

17. A scalpel according to claim 16 wherein said guard further comprises a plurality of ribs longitudinally spaced one from the other disposed along said upper surface and said side members so as to facilitate gripping the handle during use.

18. A scalpel according to claim 10 wherein said engaging surface on said handle is located on said handle such that a sufficient portion of the handle remains substantially completely exposed with the guard in the retracted position so as to allow the operator to secure the handle in one hand while shifting the position of the guard with a digit of the same hand.

* * * * *